(12) United States Patent  (10) Patent No.: US 8,968,176 B2
Altman et al.  (45) Date of Patent: Mar. 3, 2015

(54) GUIDE GLASSES

(71) Applicant: Cornfield Electronics, Inc., San Francisco, CA (US)

(72) Inventors: Mitchell A Altman, San Francisco, CA (US); William Alessi, San Francisco, CA (US)

(73) Assignee: Cornfield Electronics, Inc., San Francisco, CA (US)

( * ) Notice: Subject to any disclaimer, the term of this patent is extended or adjusted under 35 U.S.C. 154(b) by 0 days.

(21) Appl. No.: 14/074,501

(22) Filed: Nov. 7, 2013

(65) Prior Publication Data

US 2014/0088341 A1 Mar. 27, 2014

Related U.S. Application Data

(63) Continuation of application No. 12/606,104, filed on Oct. 26, 2009, now Pat. No. 8,597,171, which is a continuation-in-part of application No. PCT/US2008/061460, filed on Apr. 24, 2008.

(60) Provisional application No. 60/926,028, filed on Apr. 24, 2007.

(51) Int. Cl.
*A61M 21/00* (2006.01)
*A61N 5/06* (2006.01)
*G02B 27/01* (2006.01)

(52) U.S. Cl.
CPC ....... *A61M 21/00* (2013.01); *A61M 2021/0011* (2013.01); *A61M 2021/0027* (2013.01);

(Continued)

(58) Field of Classification Search
CPC ............. A61M 2021/0027; A61M 2021/0044; A61M 21/00; A61M 2021/0011
USPC ........................................................ 600/26–28
See application file for complete search history.

(56) References Cited

U.S. PATENT DOCUMENTS 4,315,502 A 2/1982 Gorges
5,136,555 A * 8/1992 Gardos .......................... 367/132

(Continued)

FOREIGN PATENT DOCUMENTS

CN 1068456 1/1993
EP 0412629 2/1991

(Continued)

*Primary Examiner* — Christine H Matthews
*Assistant Examiner* — Joshua D Lannu
(74) *Attorney, Agent, or Firm* — Knobbe Martens Olson & Bear, LLP

(57) ABSTRACT

A sound and light machine (SLM) produces sound and light pulses at brain wave frequencies so as to induce a particular state of consciousness in a user, while simultaneously providing music. The SLM includes light emitting diodes (LEDs) and headphone speakers. A microcontroller runs firmware to control the LEDs and headphone speakers so as to produce a plurality of dominant brainwave frequencies. Binaural voices produce a melody of music without interfering with the brainwave frequencies. Each note of the melody is sounded at a specific pitch based on information in a Tone Object, which includes a state variable index holding the note's current position within a waveform array and a state variable step, which is an amount by which to increment the state variable index at each iteration. The index is set to 0 at startup and the step is calculated from the initial note desired.

20 Claims, 5 Drawing Sheets

(52) U.S. Cl.
CPC ...... *A61M2021/0044* (2013.01); *A61N 5/0618*
(2013.01); *A61N 2005/0648* (2013.01); *A61N 2005/0652* (2013.01); *G02B 27/017* (2013.01)
USPC .......................................................... 600/27

(56) References Cited

U.S. PATENT DOCUMENTS

| | | | |
|---|---|---|---|
| 5,507,716 A * | 4/1996 | LaBerge et al. | 600/27 |
| 5,549,118 A | 8/1996 | John | |
| 5,599,274 A * | 2/1997 | Widjaja et al. | 600/27 |
| 6,071,229 A * | 6/2000 | Rubins | 600/27 |
| 6,111,522 A * | 8/2000 | Hiltz et al. | 340/932.2 |
| 7,179,979 B2 * | 2/2007 | Howarth et al. | 84/483.2 |
| 8,142,015 B2 | 3/2012 | Paolino | |
| 2005/0088611 A1 * | 4/2005 | Paolino | 351/44 |

FOREIGN PATENT DOCUMENTS

| | | |
|---|---|---|
| KR | 20-0263482 | 4/2002 |
| KR | 2002-65804 | 8/2002 |
| KR | 20-0305663 | 2/2003 |
| KR | 2007-35882 | 4/2007 |
| WO | WO2006/009771 | 1/2006 |

* cited by examiner

GUIDE GLASSES

INCORPORATION BY REFERENCE OF RELATED APPLICATIONS

All claims for domestic and foreign priority are listed in the accompanying ADS. All applications from which priority is claimed are hereby incorporated by reference.

INCORPORATION BY REFERENCE OF APPENDIX

The present specification incorporates by reference two files submitted in electronic form, which contain computer program listings. The two electronic files are entitled RevisedBIGTOE-011CP1_Firmware.txt and Revised BIG-TOE-022CP1_Firmware2.txt, which are approximately 19 kilobytes and 162 kilobytes in size; respectively. Both electronic files were saved on Oct. 24, 2013.

BACKGROUND OF THE INVENTION

You don't have to be a Buddhist monk to meditate, or a Sleeping Beauty to sleep well. Achieve these altered states of consciousness, and others, with this simple micro controller device.

The brain produces varying proportions of brain wave types, depending on its current levels of relaxation, focus, and other mental states. Each type of wave has its own characteristic frequency range, which can be read by electroencephalography.

SUMMARY OF THE INVENTION

Certain aspects of the present invention relate to a portable brain-entrainment device, such as a sound and light machine, in which the electronics and battery are embedded in a molded piece of flexible silicon that is housed in a comfortable fabric mask that wraps around the user's head, covering their eyes and ears with convex cups. The fabric mask is preferably soft and flexible. It can be attached with a strap, such as a Velcro strap to enable people with different sized heads to wear it comfortably, even if they fall asleep while wearing the device. The fabric mask can preferably be removed from the silicon piece and washed separately.

In some embodiments, the sound and light machine device produces generative, not recorded binaural music. Thus, in some embodiments, the device provides for full musical pieces, not drones, and allows for independent melodic movement in each of the parts, while maintaining a steady binaural beat and synchronized light for each of the parts.

The music can be generated as a plurality, such as four, separate binaural voices. In an embodiment having four voices, each voice can correspond to the four dominant brainwave frequencies. Each binaural voice consists of two tones and an associated LED. Thus, this embodiment of the device might be described as an eight voice digital synthesizer with embedded binaural capabilities and a synchronized light frame.

An authoring system (GG.c) can be provided to allow the designer to specify a brain-entrainment session in a text file. Multiple session files can be described. The same authoring system can allow the designer to specify a four part song in a text file. Multiple song files can be described. Any defined session file can be applied to any song. The authoring system allows the designer to specify a digitial file, such as .WAV file, which describes the waveform. In some embodiments, this file can contain a proprietary chunk defining the binaurally-active frequency (which may not be the fundamental) of the waveform. The resulting application of a session to a song, using a given waveform, is called an app. The app can be automatically converted into assembler files which provide the data for the firmware to operate on. Part of this authoring process involves the pre-calculation of 24-bit step values for each note of the song, and the pre-calculation of 24-bit fading coefficients for each change in binaural intensity of each voice.

The pre-calculations produced by the authoring system can allow for optimal performance on the target system. For instance, the implementation of one embodiment of the device can be on a 20 Mhz 8-bit microprocessor, without a hardware divide, with 8K of ROM and 256 bytes of RAM. With these limited resources the product can provide for a number of different apps. In one particular embodiment, 5 separate brain-entrainment apps can be provided, producing a total of at least 15, more preferably at least 45 minutes, of generated binaural music using a complex waveform at a playback rate of 18 Khz.

DETAILED DESCRIPTION OF EMBODIMENTS OF THE INVENTION

What would happen if you could play a recording of brain waves into someone's brain? That question popped into my mind one day while I was meditating, and it turns out that there are devices that can do this. Sound and Light Machines (SLMs) produce sound and light pulses at brain wave frequencies, which help people sleep, wake up, meditate, or experience whatever state of consciousness the machine is programmed for. The first time I tried one was a trip! Not only did I follow the sequence into a deep meditation and then out again (feeling wonderful!), but along the way I had beautiful, outrageous hallucinations.

This article shows you how to build an SLM. We'll do it the easy way, by hacking a micro controller project that already exists: Limor Fried's MiniPOV kit. This cool toy blinks pictures and words in the space you wave it through, and we can transform it into an SLM simply by changing the firmware and some minor hardware.

Many people's brain waves will synchronize to lights and sounds pulsing at brain wave frequencies, and this makes the brain change its state—a process called "entrainment." By playing sequences of pulses into your eyes and ears, you can program your brain to follow any brain wave experience you like.

We'll program our SLM to follow a 14-minute sequence that tracks the meditation experience. Since the device generates only one frequency at a time, it phases in new brain states by switching frequencies back and forth. For example, to go from fully awake to somewhat dreamy, we generate beta for a while, then alpha, then toggle between beta and alpha, reducing the duration of beta and increasing that of alpha with each iteration. Our code's brainwaveTab array defines the full sequence.

Figure 1:
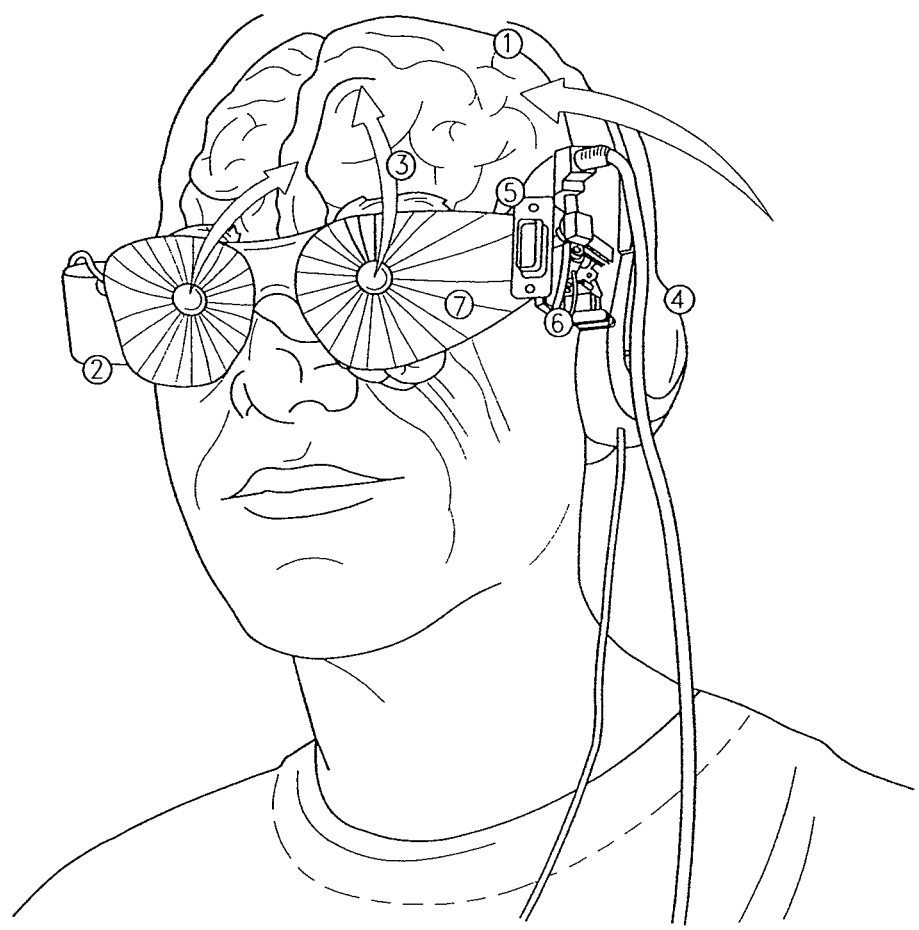
FIG. 1 shows the device in use by a wearer of an embodiment of an SLM.

FIG. 1 shows the following components of an embodiment of the guide glasses of the present invention:

1. Brain entrains to the programmed wave sequence and alters its state accordingly.
2. Battery pack powers the electronics.
3. LEDs in front of user's (closed) eyes pulse light at 2.2, 6.0, 11.1 or 14.4 Hz in order to elicit delta, theta, alpha or beta waves, respectively.
4. Headphone speakers play different tones into right and left ears to produce binaural beats (see below) that match the LED pulse frequencies.
5. Microcontroller on circuit board runs the firmware, the program that resides in the microcontroller, that controls the LEDs and headphones.
6. Serial port connector writes the firmware into the microcontroller, letting you program your own brain wave frequency sequences.
7. Graphics simply look cool.

Binaural Beats

Instead of simply playing the entraining frequency through both headphone speakers, we employ a more effective method. When we play different frequencies into each ear, the brain perceives a binaural beat frequency just as if the two tones were played next to each other on guitar strings. The beat results from the two tones cyclically reinforcing and canceling each other out, at a rate that equals the difference between the frequencies. To generate a beta binaural beat, we play a 400 Hz tone in one ear and a 414.4 Hz tone in the other. The user perceives a sound, sort of like "wah oo wah oo wah," that fades in and out 14.4 times per second.

Materials

[A] Safety Glasses
[B] Headphones
[C] Limor Fried's MiniPOV v3 kit from: store.makezine.com/ProductDetails.asp?ProductCode=MKPO VKIT, firmware downloadable with full documentation from makezine.com/10/brainwave.
[D] 1 k# resistors, ¼ w
[E] 1.0 µF capacitors bipolar
[F] 3.5 mm stero jack that mates with your headphones
[G] AA alkaline batteries (2)
[H] Kynar wire also known as 30 gauge wire-wrap wire, any 2 colors; I used blue and yellow, RadioShack #278-502 and #278-503
[I] Silicone adhesive also known as RTV (room temperature vulcanizing); clear or any other color, about $5 from your favorite hardware store
[J] Toothpicks for spreading silicone adhesive
[K] Cable ties, 10 cm long by 2.5 mm wide
[L] 10 cm length of 1.5 mm tubing
[M] Permanent or dry erase marker
[N] cellophane tape
[O] Eye graphics (optional) Download and print the template used at MAKE magazine.com/10/brainwave.
[P] Rubbing alcohol and toilet paper for removing permanent marker marks, if you make a mistake Build and Test-Program the PCB The core of our electronics is the MiniPOV v3 kit. We'll be referring to the kit's website at ladyada.net/make/minipov3.

1a. Follow the excellent instructions on the MlniPOV website to solder all the components to the included printed circuit board (PCB) except the following: LED1. LED2, LED3, LED4, RS, R6. Leave these 6 components out.

1b. Insert the two AA batteries into the battery holder and switch on. The microcontroller will run the MiniPOV firmware, and the 4 stuffed LEOs should light up.

1c. If the LEDs don't light up, then debug. Are the batteries in correctly? Check the power connections. Check for bad solder connections or solder bridges (shorts between 2 pads). Check that all LEOs, and 01, 02, and D3, are not stuffed backwards. Now we'll change the MiniPOV's firmware so you can learn how to use the development tools and see how easy it is.

1d. Download and install the AVRDUDE software needed for your operating system. Links for the software are on the MiniPOV website listed above, under "Download." If you're using a USB/Serial adapter, also download the USB/Serial converter driver.

1e. Create a folder on your computer called slm. Download the firmware for MiniPOV from the MiniPOV website into the slm folder and unzip it. Using a text editor, open up the mypov.c file, and change the pattern in the image array (near the top of the file) to the pattern at right. Since a 1 will light up an LED and a 0 leaves it off this will create a pattern on 4 LEDs that looks something like "VVVVV" when, you wave the Mini-POV back and forth through the air. Switch off the MiniPOV's battery pack, plug the MiniPOV into your computer's serial port. and switch it back on.

1f. Compile and program the microcontroller by following the instructions on the MiniPOV website for your operating system. Under VVindovvs, you'll enter the following (at right) into a command window. Turn the MiniPOV power pack off and unplug the PCB from the serial port. Switch the power back on and the 4 LEOs will light up. Wave it around. and behold the VVVVV pattern you just programmed in!

NOTE: Adding the capacitors creates low-pass filters that smooth out the square waves into sine waves, for more pleasing audio.

Make the SIM Controller

Figure 2:
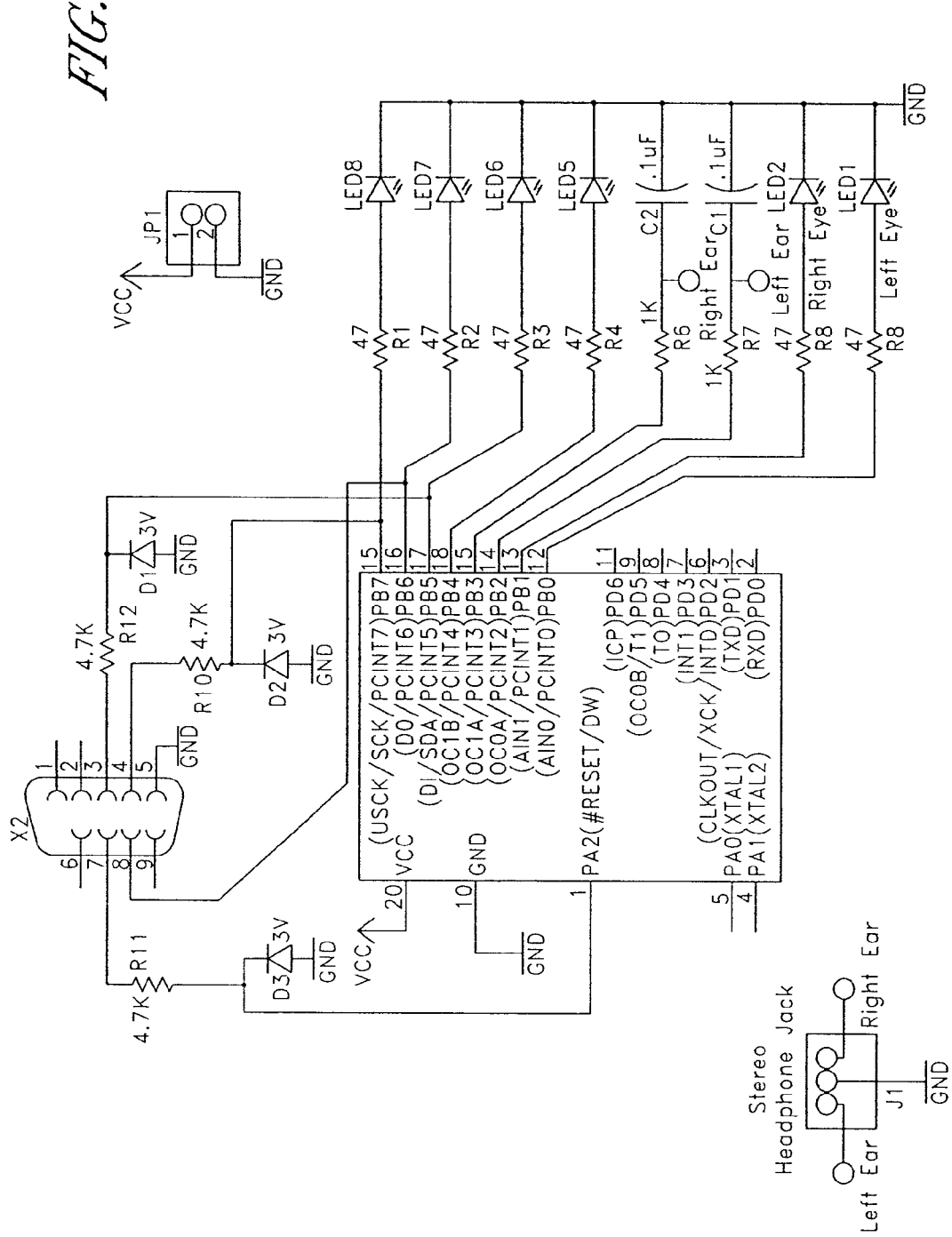
FIG. 2 is a schematic showing the configuration of an embodiment of an SLM.

A complete schematic for the SLM as hacked from the MiniPOV is available at makezine.com/10/brainwave and is provided at FIG. 2. R5/C2 and R5/C1 are each low pass filters for converting the square wave output of the microcontroller to sine waves (more or less). Here is the math: We want the cut off frequency (Fc) of the low pass filter <half 400 Hz tone we'll be using: $Fc=1/(2*Pi*R*C)=1/(6.26*1000*0.0000001)=160$ Hz. This works because a 400 Hz square wave can be modeled as a 400 Hz sine wave with lots of multiples of this frequency added to it. The LPF greatly diminishes the volume of all frequencies greater than 400 Hz, leaving the 400 Hz sine wave untouched.

2a. Download SLMfirmware.zip from makezine,com/IO/brainwave into your slm directory and unzip it. Let it overwrite the makefile with the new one if asked. Program the microcontroller with the new firmware. Follow Step 1e above to hook it up to your computer. Then compile and upload the firmware to the microprocessor. The process is identical to Step 1f, but we're programming slm instead of mypov. Under Windows, you'll enter the code seen to the right.

2b. Turn off and unplug the MiniPOV, which is now an SLM controller, although it won't do much, since we don't have any outputs hooked up yet. Solder the two IJIF capacitors into the pads for LED3 and LED4. Solder the two 1 kD resistors into the pads for R5 and R6. Clip the excess leads on the back of the PCB.

2c. Cut a 2" length of blue wire for hooking up the stereo headphone jack (for ground) Cut two 2" lengths of yellow wire. Strip ⅛" off one end of each wire. and tin.

2d. Place the stripped end of the blue ground wire into the head; The jack's ground terminal and solder. Place one of the yellow speaker wires into one of the jack's empty terminals and solder. Do the same for the remaining speaker wire.
NOTE: There are three terminals on the headphone jack. One is ground, offset from the others, and the other two are for the left and right speakers. For this project, it does not matter which way we connect the left and right speakers.

2e. Twist these 3 wires neatly, but leave about W' untwisted. Cut them so that they all extend the same length, strip 1132" off each, and tin. Solder the ground wire (blue) to the PCB trace that connects all of the LEO grounds together Then solder the right and left speakers (yellow) to the outputs for LED3 and LED4.

2f. Test the audio by plugging your headphones into the jack, putting them on, and flipping the power switch. You should hear some spacey sounds in both ears. If not, the most likely problems are bad solder connections or solder bridges.

3. Prepare the Battery Pack

3a. Unsolder the 2 battery pack wires from the PCB.

3b. Cut two 4" lengths of wire (one yellow. one blue). strip 3 mm off one side of each, and tin the stripped ends.

3c. Hold the blue v; lire to the black battery pack wire (negative) and solder them together. Slip 12 mm of heatshrink tubing over the connection and lightly rub the tubing back and forth on all sides with the soldering iron for a few seconds until the tubing shrinks around the connection. Repeat for the red battery pack wire (positive), but use yellow wire to extend it.

4. Prepare the Glasses

4a. The glasses need 1 LED facing each eye. Place the glasses on your face. look straight ahead, and point ttle tip of a marker at your right eye. Slowly move the marker toward your eye to make a mark directly in front of your eye. Repeat for left eye. If you want to cover the glasses with cool graphics. trace the shape of each lens onto a piece of paper, and cut the 2 templates out for later.

4b. Use a small sharp nail to make a pilot indention Into the 2 marks on the glasses. Drill a 4.5 mm hole for each eye, taking care not to let the bit slip. Testflt the leftover LEOs from the MiniPOV kit into the holes. If you can't push them all the way in, enlarge the holes a little by pushing the sides against the spinning drill bit.
NOTE: The marks on the glasses should be somewhat symmetrical If not, use some toilet paper and rubbing alcohol to remove the marks and try again.

4c. Push an LED into each eye hole so that they will face your eyes when you wear the glasses. Cut four 8" lengths of wire (2 yellow, 2 blue). strip Vs" off one side of each. and tin the stripped ends.

4d. The longer lead of each LED is the positive lead. Cut off all but ⅛" of the positive leads for each LED, tin them, and solder ttlem to 8" yellow wires.
Do the same for the negative leads, soldering them to the blue wires.

4e. Bend the wires on both LEDs up and over the top edge of the glasses and glue each LED into place from the outside using silicone adhesive. Use a toothpick to create a solid hemi. sphere of silicone that makes good contact with the glasses and coats the LED leads and exposed wire. Let the adhesive hal'den (1-2 hours).
NOTE; Silicone adhesive is a good choice for electronic projects because it does not conduct electricity and it is easy to use.

Attach the Battery Pack and PCB

5a. Prepare 2 pairs of cable ties by slipping one about 18 mm through the other.

5b. Spread silicone adhesive 2%" along the right temple of the glasses to span the length of the battery pack, Press the battery pack into the adhesive and secure with the double cable ties. Trim the excess length off the cable ties. Then see Step (5h TK).

5c. Route the 4 wires from the LEOs and 2 from the battery pack along the top of the glasses toward the left temple (where they will connect to the PCB), twisting them together along the way. Keep the 2 wires from the battery pack together. so you don't confuse them with the LEO wires.

5d. Hold the PCB in place on the left temple (but don't glue yet), positioning it such that the connector sticks forward of the left lens when the glasses are unfolded. This will let you plug the glasses into your computer. Trim the 6 wires so that there will be only a little bit of slack when they connect to the LEDs and battery pack. Strip 1.5 mm off the end of each of the 6 wires, and solder them to the unstuffed LEO and battery pack contacts, maintaining proper polarity.

5e. Spread silicone adhesive along the left temple of the glasses for the length of the PCB. Press the PCB into the adhesive and secure with another cable tie pair. Remember that the connector needs to plug into your computer's serial port without the glasses getting in the way. Clip any excess wire under the PCB and cut the excess off the cable ties, 6. Secure the Headphone Jack and Loose Wires 6a. Push the wires to the side. put a blob of silicone over D2 and R11 on the PCB. and push the headphone Jack sideways into the blob. Add more adhesive with a toothpick to completely cover the terminals of the jack and about the first 3 mm of each attached wire.

6b. To hold the loose wires in place while they are being glued. prepare eight 4" strips of magic tape by folding a small bit of each end over to stick onto itself. Stick the tape pieces where you can reach them while gluing in the next step.

6c. Use a toothpick to thinly spread silicone adhesive between tile wires and along the top of the glasses. then glue the wires along the glasses. Use the tape stnps to keep the wires in place while the adhesive hardens. Also tape the headphone jack in place.
Wait for the adhesive to harden. about 1-2 hours, then remove the tape.

7. Apply Cool Graphics (Optional)

7a. Using the templates you created earlier, cut out lens-shaped pieces from your graphics for the left and right lenses: Cut a hole in each one where the back of the LEOs will poke through.

7b. Apply a very thin layer of silicone adhesive (spread with your finger) in a horizontal strip on the back of each cutout. Affix them to the front of the glasses. Now they look cool!

Now go Use it

Get comfortable, put on the glasses and headphones, close your eyes (the LEDs are bright!), and flick the power switch. Enjoy the hallucinations as you drift into deep meditation, ponder your inner world, and then come out after the 14 minute program feeling fabulous. New to meditating? Here are a few ideas. Breathe normally and pay attention to your breathing. If you space out, no worries—just focus on your breathing again. Or don't focus on anything: follow your thoughts wherever they go. You can also concentrate on something before you start, solving a technical problem, exploring a difficult decision, feeling through the issues in a relationship. If you space out, just refocus on your intent. There is no end to the variety of what you can do in a meditative state.

Cautions: Blinking lights should be avoided by anyone prone to seizures. If you are sensitive to seizures, please disconnect the LEDs in this project; your brain can effectively entrain with the binaural beat audio alone. Certain conditions, such as ADHD, can worsen with theta and delta entrainment. Please discontinue using this SLM if you experience any problems.

Programming Your Own Brain Wave Sequences

You can program your own sequence by editing the brainwaveTab definition in the file slm.c. Each line defines a pair (bwType. bwDuration) that sets the brain wave type for an amount of time, specified in tenthousandths of a second. For example, the first pair, {'b', 600000}. runs the beta frequency (14 AHz) for 60 seconds You can program the session to last longer than 14 minutes, spending more time in deeper states.

To aid sleep, you may also want to decrease the pitch of the audio, since lower pitches are more relaxing. Vou can do this by tweaking the OCRDA setting in main and the OCR1A settings in the function do_brainwave_element also in the file slm.c. Explore and enjoy!

Firmware Documentation

Firmware is the computer program that controls a microcontroller. [Why not call it software? Firmware is somewhere between software and hardware—it is a software that directly controls hardware]. In this project we converted the MiniPOV into a Sound & Light Machine (SLM) simply by changing the firmware, along with some minor hardware changes.

This document is intended to teach you enough about the SLM firmware to be able to create your own brainwave sequences. The next section ("Overview of the SLM firmware") is all you really need to read. But if you are interested in learning more about how the firmware works, I have also given plenty of extra detail.

Firmware is actually a bunch of lines of text in a file, written with a text editor. Collectively the lines of text tell the microcontroller exactly what to do. To program the microcontroller with the firmware it is convenient to use a special script file called a "makefile." (For this project, the makefile runs a C compiler, an assembler, a linker, an object converter, and programming software—but you don't really need to understand any of this since the makefile does everything for you.)

Overview of the SLM Firmware

The microcontroller for the SLM comprises most of the hardware for the SLM, and is used primarily as a timing device to output square-waves that pulse LEOs in front of each eye and speakers for each ear. The SLM firmware tells the microcontroller exactly how to create a sequence of these square-waves for blinking LEOs and pulsing speakers at brainwave frequencies. The sequence of square-waves mimics the sequence of a brain's frequencies as it goes into desired states of consciousness. The SLM firmware that I wrote generates a sequence that starts from a state of being awake, goes into deep meditation, hangs out there awhile, and then into being awake again (feeling wonderful).

The SLM's brainwave sequence is determined by a table caiied the "Brainwave Table" at the beginning of the SLM firmware. The Brainwave Table contains several "Brainwave Elements". Each Brainwave Element consists of a "Brainwave Type" (Beta, Alpha, Theta, or Delta) and a "Brainwave Duration" (which is how long to play this Brainwave Type, before doing the next Brainwave Element in the table). To change the SLM's brainwave sequence, simply change the Brainwave Table in a text editor, save the file, and run the makefile (as described in the article).

The Brainwave Table on page 8 is an easy-to-read representation of the actual table in the firmware that I created for the meditation sequence. The actual table in the firmware is shown on pages 12 and 13, called "brainwaveTab". You can see how it correlates to the more readable one on page 8. 'b' is for Beta, 'a' is for Alpha, 't' is for Theta, and 'd' is for delta. The last element must have '0' for its brainwave Type (to tell the firmware that it reached the END of the table). The times to play each brainwave (the Durations) are given in units of $\frac{1}{10}$ milliseconds_divide the desired durations by 10,000 to get these values in brainwaveTab.

CAUTION: Please do not use the SLM if you are, or think you may be prone to seizures. Also, please be aware that certain conditions, such as ADHD, can worsen by entraining to lower brainwave frequencies. If you experience any problems, please discontinue using this SLM.

The above is really all you need to know to create your own brainwave sequences.

The rest of this document gives more in-depth explanation of how the SLM firmware does its thing.

Some words about the microcontroller

The microcontroller used in this project is the ATTINY2313, made by Atmel. It is part of their AVR family of microcontrollers. The datasheet for this chip can be downloaded from Atmel's website:

NTP://www.atmel.com/dyn/resources/proddocuments/doc2543.pdf

Although many different microcontrollers are well suited for performing the tasks necessary fora Sound & Light Machine, the Atmel AVR family of chips has many advantages. One of them is that there is no need to buy a programmer for these chips, since it has a built in programmer_all you need is a computer with a serial port (or a USB connector and an inexpensive USB-to-serial converter) and some software. Another advantage is that all of the software necessary for programming the chip is free and open source. A free C-language compiler is available, so no one needs to learn the AVR assembly language [Assembly language is the low-level language that microcontrollers understand and that all firmware used to be written in. Each micro controller family has its own firmware language. When you compile a C program a compiler creates assembly language that the micro runs. Well, that's not quite accurate—actually, assembly language is for (very geeky) humans, whereas the micro runs on machine language, which is the binary numbers stored in program memory that the assembly language represents. There is another piece of software called an assembler that converts assembly language to machine language]. Another really wonderful advantage is that there is a user forum called AVR-freaks.org that, 24/7, is full of geeks that love answering questions you may have about using the AVR family of micros. Being new to AVR chips, I made use of the user forum when I came up against a problem I needed help with. At 11 pm I posted my question, and by 11:30 pm someone pointed me to info where I could solve my problem. Sweet!

Most software for designing hardware and creating firmware is made for PCs running Windows. Another nice aspect of using A VR chips is that all of the software needed is available for Windows, Mac OS, and Linux.

Brainwave Frequencies the SLM firmware will generate

Brains generate brainwaves across a frequency spectrum. The spectrum is divided into four bands: Beta, Alpha, Theta, Delta. [More recently a fifth brainwave band has been added: Gamma, but we are sticking with the original four for this project, since they are more well understood, and we can accomplish a lot with just these four.] For the SLM I have chosen one frequency for each Brainwave Type. See the table on the next page:

| Type | Band | Frequency used in SLM | Associated States |
|---|---|---|---|
| Delta waves | 1'2 Hz to 4 Hz | 2.2 Hz | deep unconscious, intuition and insight |
| Theta waves | 4 Hz to 8 Hz | 6.0 Hz | subconscious, creativity, deep relaxation |
| Alpha waves | 8 Hz to 13 Hz | 11.1 Hz | spacey and dreamy, receptive and passive |
| Beta waves | 13 Hz to 30 Hz | 14.4 Hz | conscious thought, external focus |

Generating Square-Waves with the Microcontroller
LED Square-Wave Timing

The square-waves for pulsing the LEOs for each eye are generated by a timing loop in the firmware. Within this timing loop the firmware manually toggles microcontroller output pins. ["Toggling" means: if the output pin was High, clear it to Low; and if the pin was Low, set it to High.] Each LED is connected to an output pin on the microcontroller. The firmware toggles these output pins together, so that the LEOs connected to these output pins will pulse exactly the same.

As an example of how the LED timing works, let's say that we wish to blink the LEOs for the eyes at the Beta frequency of 14.4 Hz. This means that the LEOs at each eye should blink High and Low 14.4 times per second. This means that the LED should toggle High and Low every 0.0347 seconds (which is 34.7 milliseconds, or 34.7 ms).
Here's the math:
The Duration of the LED blinking High and then Low (one cycle, or the "period"): 1/14.4 Hz=0.0694 sec=69.4 ms
The duration for 1'2 the period (this is the duration of the High and the duration of the Low): 69.4 ms 12=34.7 ms
Since the microcontroller's datasheet tells us how long it takes for the microcontroller to perform each instruction, we can write a loop of code that does nothing but delay for this length of time. Then, to toggle the LED at the Beta frequency, we turn the LED on (by setting the output pin of the microcontroiier to High), delay for 34.7 ms, and then turn the LED off (by clearing the output pin to Low), delay for 34.7 ms, and repeat this process.

Speaker Square-Wave Timing

We could do a similar thing for the audio, but the timing would get complex, since the brainwave audio should be binaural beats (as explained in the SLM article), rather than simply pulsing at brainwave frequencies. Fortunately, the microcontroller has some built-in functionality that greatly simplifies our task of creating the binaural beat frequencies at the speakers.

The microcontroller used in the SLM project has two hardware timers built into it. The SUv1 firmware makes use of these two timers to create the binaural beats. One timer, called Timer 0 (or TO), is set up to generate a Base Frequency of about 400 Hz that is fed into one ear's speaker. The other timer, called Timer 1 (or T1), is used to generate Offset Frequencies that are fed into the other ear's speaker. When the Offset Frequency in one ear is heard together with the 400 Hz in the other ear, the listener hears a beat frequency of the desired brainwave frequency. To get a beat frequency of 14.4 Hz, T1 is configured to output about 414.4 Hz.

Once the firmware starts TO and T1, they will generate square-waves on their own, without firmware intervention, until the firmware tells the timers to stop.

The Microcontroller's Hardware Timers (Details)

Here are the nitty-gritty details of how the firmware sets up the microcontroller's two hardware timers to output binaural beats.

Both of the timers in the microcontroller can be set up in various modes, according to the specifications in the microcontroller's data sheet. To create square-waves for the sound that feeds into the headphones, the firmware sets up the timers in a mode that toggles each timer's output pin for every time the timer times out (explained more, below). The datasheet calls this CTC mode (which they say stands for Clear Timer on Compare Match). In this mode, there is a Compare Register where the timing value is stored. The Timer counts upward from 0, one count for each clock (more on the clock, below). When the Timer reaches the value in the Compare Register (which is called "timeout"), the output pin for the Timer is automatically toggled, and the timer starts counting upward from 0 again. The clock frequency is determined by the clock of the microcontroller and the Prescaler. In this project, we use the microcontroller's internal clock oscillator, which is set up to run at 8.0 MHz. This frequency can be divided down by a Prescaler, which can divide by powers of 2: 1, 2, 4, 8, etc., up to 256. The formula for determining the output square-wave frequency, Fo, for the timer's output pin for this mode (as given in the datasheet) is:

$$Fa = Fclk/(2*P*(1+C))$$

where
Fclk=
8,000,000 Hz P=
Prescale value
C=Compare Register value
Fa=output square-wave frequency
Each timer (TO and T1) can be set up independently. Each has its own output pin.

As an example, let's see how to use the two timers to generate Beta binaural beats. To generate the Base Frequency of about 400 Hz, TO is used with TO Prescale=256 and TO Compare Register=38, resulting in Fa=400.641 Hz (this is the closest we can get to 400 Hz). The Offset Frequency for binaural beats is generated in T1, with T1 Prescale=1, and T1 Compare Register=the appropriate value to generate the Brainwave Type. To get a binaural beat of about 14.4 Hz (the Beta frequency), we need to set T1 to output 14.4 Hz higher than the frequency of TO, which comes to 415.041 Hz. Using the above formula to get as close as we can to 415.041 Hz, we set the T1 Compare Register to 9637, giving an output frequency of 415.024 Hz. The perceived beat frequency will be:

415.024 Hz–400.641 Hz=14.383 Hz which is pretty close to 14.4 Hz.

Given a Base Frequency of 400.641 Hz (generate on TO), below is a table which shows the value of the T1 Compare Register for creating an Offset Frequency as close as we can get for each of the four Brainwave Types ("OCR1A" is how the datasheet abbreviates the T1 Compare Register). See the table on the next page:

| Type | OCR1A | Offset Frequency Fo | Difference 400.641 Hz Base |
|---|---|---|---|
| Delta waves | 9928 | 402.860 Hz | 2.219 Hz |
| Theta waves | 9836 | 406.628 Hz | 5.987 Hz |
| Alpha waves | 9714 | 411.734 Hz | 11.093 Hz |
| Beta waves | 9637 | 415.024 Hz | 14.383 Hz |

Timing the LEOs and Speakers Together

To playa given Brainwave Type for a certain Duration, the firmware starts TO at the Base Frequency of 400.641 Hz (which goes to one speaker), then starts T1 at the Offset Frequency for the given Brainwave Type (which goes to the other speaker), and the user hears the binaural beats for the given Brainwave Type. The firmware then keeps T0 and T1 going for the given Duration (the timing for the Duration is accomplished by a delay loop, which is described in the next paragraph). This takes care of the sound. What about the blinking lights?

Recall earlier that we would use a delay loop for creating the square-waves for blinking the LEOs. We can use this same delay loop for waiting the specified Duration for the given Brainwave Element. Cool, yes? While the hardware timers are playing the binaural beats, we just keep blinking the LEOs with the timing loop for the given Duration. Then we've accomplished creating binaural beats for a given Brainwave Type, along with blinking lights at the same Brainwave Type, played for a given Duration.

An example should make this clear. If we want to play Beta frequencies for 60 seconds, the firmware does-the following:
Start T0 to toggle one ear at the Base Frequency of 400.641 Hz
Start T1 to toggle the other ear at the Offset Frequency of 415.024 Hz Manually toggle the LEOs at each eye at 14.4 Hz using the delay loop Keep manually toggling the LEOs until all of the delays in the delay loop
add up to 60 seconds (how to do this will be described later)
After the Duration of 60 seconds is over, the firmware could then stop manually toggling the LEOs to turn off the lights, and then turn off T0 and T1 to stop the sound at the speakers. Or, the firmware could start a different brainwave frequency playing at the LEOs and speakers for another Duration.

Generating a Brainwave Sequence with SLM Firmware

The sequence of Brainwave Elements in the Brainwave Table is what determines the brainwave sequence generated by the SLM.

The firmware starts by playing the first Brainwave Element from the Brainwave Table. It does this (as described above) by starting T0 at the Base Frequency, starting T1 at the Offset Frequency for the Brainwave Type (given in the Brainwave Element), and allows the timers to continue for the Duration (given in the Brainwave Element) while blinking the LEOs at a rate for the given Brainwave Type. Then (leaving T0 playing the Base Frequency) it grabs the next Brainwave Element from the Table, sets up T1 for the new specified Brainwave Type and plays it, along with blinking the LEOs at the new Brainwave Type's frequency, and plays it for the new specified Duration. Then (leaving T0 playing the Base Frequency) it grabs the next Brainwave Element from the Table. Etc.

This process continues till there are no more Brainwave Elements in the Brainwave Table. Then the firmware turns off both T0 and T1, stops manually toggling the output connected to the LEOs, and puts the microcontroller into a low-power mode.
(An easy-to-read representation of the Brainwave Table I created for the meditation sequence is shown on page 8.)
We can state the above more concisely by being a bit more geeky about it:
Initialize hardware and variables
start Timer 0 with Base Frequency into speaker #1
Do
get next Brainwave Element (consisting of Type and Duration) from brainwaveTab start Timer1 with binaural beat Offset Frequency for Brainwave Type into speaker #2 blink LEOs at brainwave frequency for the Brainwave Type
and wait for the specified Duration
Until end of brainwaveTab
stop Timer 0 and Timer 1 to stop sound at both speakers turn off LEOs
put microcontroller to sleep (low-power mode)

Let's get a little bit more geeky, and state things more in the way our specific microcontroller likes to see things (according to the datasheet). First of all, here is how the hardware is set up:
1 LED for each eye:
    LED #1: PB0 (pin 12) LED #2: PB1 (pin 13)
1 speaker for each ear:
    speaker #1: OC0A/PB2 (pin 14) speaker #2: OC1A/PB3 (pin 15)
And here is the algorithm for the firmware:
Main:
Initialize
    set Port B for outputs (0ORB=0xFF)
    setup Timer 0 for CTC mode and for toggling OC0A (which is Timer O's output pin) start Base-Frequency square wave=400.641 Hz on Timer 0 (Prescale=256, OCR0A=38) to output sound to OC0A (connected to speaker #1). setup Timer 1 for CTC mode and for toggling OC1A (which is Timer 1's output pin) (Prescale=1, OCR1 A not set yet)
MainLoop:
    get next brainwaveElement (which consists of a brainwaveType and a brainwaveOuration) if brainwaveType=0, then quit the MainLoop (when brainwaveType=0 we are done) otherwise, do the following:
    start T1 square wave=binaural beat offset for the brainwaveType
        (OCR1A=Offset Frequency for brainwaveType) to output sound to OC1A (connected to speaker #2)
    loop to blink LEOs at PB0 and PB1 at correct timing for the
    brainwaveType keep looping for brainwaveOuration
endofMainLoop
stop Timer 0 and Timer 1 to stop sound at both
speakers turn off both LEOs
put processor to sleep (low-power mode)

The actual firmware is given starting on page 11. It is described in more detail starting on page 9.

How to Specifyabrainwave Sequence for this SLM
    CAUTIONS: BLINKING LIGHTS SHOULD BE AVOIDED BY ANYONE PRONE TO SEIZURES. If you are sensitive to seizures, please disconnect the LEDs in this project (your brain will effectively entrain with the binaural beat audio alone). CERTAIN CONDITIONS, SUCH AS ADHD, CAN WORSEN WITH Since we can only generate one brainwave frequency at a time in this SLM project, we need to create a brainwave sequence that tries to keep your brain active at various brainwave frequencies by going back and forth between two brainwave frequencies. For example, if we want to go from fully awake to somewhat dreamy, we would generate Beta for awhile, then Alpha for awhile, and go back and forth between Beta and Alpha, but reducing the length of Beta and increasing the length of Alpha with each iteration.

Another thing to keep in mind when creating your own brainwave sequence is to start by meeting your user where they are at and then take them where they want to go. For example, if you want to create a sequence to bring people to sleep, then start with being awake and conscious (Beta), then, after awhile, start adding some spaceyness (Alpha).

The brainwave sequence for meditation that I created uses the above techniques. The Brainwave Table for it is given on the next page.

| Brainwave Table (Meditation sequence) | | |
|---|---|---|
| Element number | Brainwave Type | Brainwave Duration (sec.) |
| 1 | Beta | 60 |
| 2 | Alpha | 10 |
| 3 | Beta | 20 |
| 4 | Alpha | 15 |
| 5 | Beta | 15 |
| 6 | Alpha | 20 |
| 7 | Beta | 10 |
| 8 | Alpha | 30 |
| 9 | Beta | 5 |
| 10 | Alpha | 60 |
| 11 | Theta | 10 |
| 12 | Alpha | 30 |
| 13 | Theta | 20 |
| 14 | Alpha | 30 |
| 15 | Theta | 30 |
| 16 | Alpha | 15 |
| 17 | Theta | 60 |
| 18 | Alpha | 15 |
| 19 | Beta | 1 |
| 20 | Alpha | 15 |
| 21 | Theta | 60 |
| 22 | Delta | 1 |
| 23 | Theta | 10 |
| 24 | Delta | 1 |
| 25 | Theta | 10 |
| 26 | Delta | 1 |
| 27 | Theta | 30 |
| 28 | Alpha | 15 |
| 29 | Beta | 1 |
| 30 | Alpha | 15 |
| 31 | Theta | 30 |
| 32 | Alpha | 15 |
| 33 | 8eta | 1 |
| 34 | Alpha | 20 |
| 35 | Beta | 5 |
| 36 | Alpha | 20 |
| 37 | Beta | 15 |
| 38 | Alpha | 15 |
| 39 | Beta | 20 |
| 40 | Alpha | 10 |
| 41 | Beta | 25 |
| 42 | Alpha | 5 |
| 43 | Beta | 60 |
| 44 | END | Total = 856 sec (about 14% min) |

Description of the Actual SLM Firmware

I'll start the description with the Brainwave Table (somewhat near the top of the firmware). It is called "brainwaveTab" in the firmware. The brainwaveTab contains several lines, each of which is a "brainwaveElement". Each brainwaveElement consists of a bwType ('b' for Beta, 'a' for Alpha, 't' for Theta, 'd' for Delta) and a bwDuration (which is expressed in an odd time—to get seconds, divide the number by 10,000). The last brainwaveElement must have '0' for its bwType to indicate the END of the brainwaveTab.

Now let's look at the bottom of the firmware to the "main" function. The main function starts by initializing the hardware registers of the microcontroller: no interrupts [interrupts are a way for hardware to call a function when an event happens—we aren't using interrupts in the SLM firmware], set all pins to outputs, and make sure that all of these output pins are Low. Then start TO to output the Base Frequency using CTC mode, toggling output pin OC0A (connected to speaker #1). Then set up T1 to output the Offset Frequency (but we won't start T1 here—we start T1 in the dO_brainwave_element function, as described in its paragraph, below). Then there is a loop that grabs each brainwaveElement in brainwaveTab, sending each brainwaveElement to the dO_brainwave_element function to do the work. The loop finishes if it finds a brainwaveElement with a bwType of '0'.

Once we've gone through the entire brainwaveTab, the firmware stops TO and T1 (to stop the sound), enables sleep-mode (which will put the micro into a low-power mode), waits 1 second (to let things settle—this is way longer than necessary, but that won't hurt anything), turns off all output pins, makes all pins inputs (since this uses less battery power), and then puts the micro to sleep.

OK, now look back to the top of the firmware. The "include" statements at the beginning let the C compiler know where to look for some code that is pre-written, and comes with the compiler (these are known as library functions).

The "define" statements that come next define some constants used for the microcontroller's hardware timers.

Next comes the Brainwave Table, described earlier.

Next comes the delay loop function, "delay_one_jenth_jns". All it does is go around a loop a specified number of times, performing, no useful task except to delay for the correct amount of time. It delays for a given number of 0.1 ms ($\frac{1}{10}$ millisecond). So, for example, to delay 60 seconds, the input to this routine should be 600,000. One thing a little odd about this routine is that I had to tell it to do something; otherwise the C compiler would see that it didn't actually perform any useful task, and it would "optimize" the code away (this is because the C compiler we are using is an "optimizing compiler"). in the delay loop I told the microcontroller to toggle an output pin in Port O (which we don't use), which forces the compiler from optimizing the loop into non-existence. The function uses a constant called "OelayCount". I chose the value of OelayCount=87 by trial and error so that the function delays very close to increments of $\frac{1}{10}$ ms.

The next function is called "blink_LEOs". It has 3 inputs, and it does what the name implies. And it does it at a giv'en timing, and for a given Duration (all given in units of $\frac{1}{10}$ ms). Rather than create a square-wave with equal High times and Low times, the function can make a squarewave with a specified High time (called "on'Iime") and a different Low time (called "offTime"). The function turns on the LED, waits on Time (by calling delay_one_tenth_ms), turns off the LED, and waits offTime (by calling delayone_fenth_jns). It does this in a loop until the specified duration is reached. The number of times to go through the loop is calculated by dividing the specified duration by on Time+offTime. Let's look at an example to see how this works: if we want the LEOs to blink at Beta Frequency of 14.4 Hz for 60 seconds, then duration=600,000, on Time=347, and offTime=347. Each run through the loop takes 34.7 ms+34.7 ms=0.0694 seconds, so we want to run through the loop for 600,000/(347+347)=864 times (truncated to an integer). The total time will be: 864*0.0694 sec=59.96 sec, which is pretty close to the specified 60 seconds duration.

The next function is "do_brainwave_element". It has one input, telling it which brainwaveElement to play. (Keep in mind that in the C language, the first element of a table is 0, rather than 1.) This function grabs the specified brainwaveElement from the brainwave Tab, and gets the brainwaveElement's bwType and bwDuration. The function contains one section for each of the four Brainwave Types. Each section is very similar. For example, let's look at the section for Alpha (bwType='a'). It sets the output compare register for T1 (which is called "OCR1A"), to 9714, to start T1 with an Offset Frequency of 411.734 Hz to create a binaural beat for the user at 11.1 Hz (which is Alpha waves). Then it calls the blink_LEOs function with the correct on Time and offTime and total Duration to make the LEOs blink at Alpha frequencies for the given length of time. Here's the math for the LED blink-rate:

onTime = 451 (0.0451 seconds) offTime
= 450 (0.0450 seconds)

So the LEOs blink on and off at this rate:

$$1(0.0451+0.0450)\text{sec}=11.1 \text{ Hz (which is Alpha waves)} \qquad (1)$$

Here is a table of values for each Brainwave Type:

| Type | OCR1A | Offset Frequency Fo | Binaural Beat Frequency | onTime | offTime | LED blink Frequency |
|---|---|---|---|---|---|---|
| Delta waves | 9928 | 402.860 Hz | 2.219 Hz | 225.3 ms | 225.3 ms | 2.219 Hz |
| Theta waves | 9836 | 406.628 Hz | 5.987 Hz | 83.5 ms | 83.5 ms | 5.988 Hz |
| Alpha waves | 9714 | 411.734 Hz | 11.093 Hz | 45.1 ms | 45.0 ms | 11.099 Hz |
| Beta | 9637 | 415.024 Hz | 14.383 Hz | 34.7 ms | 34.7 ms | 14.409 Hz |

You can see from the above table that for each brainwave type, dO_brainwave_element is able to blink the LEDs at a rate that is very close to the binaural beat frequency.

The final function is the main function, which was described earlier.

And that is it. Except for one gotcha. Whiie I was creating the firmware, to make it easier to debug I used a small brainwaveTab with only 5 brainwaveElements. Eventually I got the firmware to work great with this small brainwaveTab. But then when I created the full brainwaveTab, the firmware didn't work. What the?! After trying to figure out why the firmware would not work with the full-sized brainwaveTab, I finally formulated a question and posted it to the AVR user forum mentioned earlier. I got my answer within 30 minutes. It turns out that the C compiler tells the microcontroller to transfer the whole brainwaveTab structure to RAM when the firmware starts up. And that can not work because the microcontroller's RAM is only 128 bytes_and the brainwave Tab is way bigger than 128•bytes. The solution is to use some library functions (pgm_read_byte and pgm_read_word) and a macro (PROGMEM) that come with the C compiler. With these in place the firmware will not transfer brainwaveTab to RAM, but leaves it in program ROM—and the firmware works great! (This is described in the actual firmware, on page 12.)

The following pages show the complete firmware. You can download this firmware in its own file (with the makefile), called "slmFirmware.zip", from the makezine.com website where you downloaded this document.

Brain Machine II

A more complex SLM with many improvements to enhance relaxation and entrainment. It gently fades sound and lights in and out, handles multiple simultaneous frequencies, matches brain wave types to different colored LEDs and binaural base frequencies, masks the binaural, and beats with music or other sounds. Physically, it fits in a soft fabric sleep mask and uses a light, flexible, rechargeable battery. It has other enhancements as well.

"GuideGlasses" is the internal name for one embodiment of a Brain Machine II electronic brainwave device. The firmware is written in Zilog Z8 assembly language. The source code for this firmware is included later in this application.

Introduction

This firmware was initially developed using C language software running on DOS on a PC, and then converted to Zilog Z8 assembly language.

The original C language software listing is included later in this document. This original development software includes some elements that are not included in the latest version of the Z8 finnware. These elements will be included in the final version of the finnware.

The software creates sound and light, pusling at brainwave frequencies. The sound consists of up to four pitches in each ear, one pitch per brainwave type (Beta, Alpha, Theta, and Delta), creating a musical chord, similar to a drone in Indian music. The light consists of four different colored LEDs in front of each eye, a different color for each brainwave type.

Each pitch in the musical chord uses an audio file as a sample to create a pleasing sound for the user, one that masks the harsh sounds of the brainwave frequencies. For each pitch, there is the standard pitch in one ear, and a pitch with an offset frequency in the other ear. The offset frequency is different from the standard pitch by a specific amount depending on the brainwave type:

Beta 26.0 Hz
Alpha 11.0 Hz
Theta 6.0 Hz
Delta 2.25 Hz

The standard pitches together with the offset pitches create binaural beats that the user will perceive and that will induce their brain to entrain to the brainwave type. These brainwave types can be faded in and out, making it easy on the user to entrain to the brainwave types coming in and out.

The reason that there are four pitches, one for each brainwave type, is that this makes it easier for the user's brain to entrain to each brainwave type, even if the four brainwave types are fading in and out independently.

Each LED pulses sinusoidally at the same rate and in phase with the binaural beat sounds. There are four colors for the LEDs for each eye:

Beta Blue
Alpha Green
Theta Yellow
Delta Red

The sinusoidal pusling for each colored LED for each eye are exactly the same. The exact colors are not important, but there is a correlation between the frequency of the light and the frequency of the brainwave type it is for. Since Beta is the highest frequency brainwave type we are using, it uses the highest frequency LED (blue). Delta is the lowest frequency brainwave type we are using, so it gets the lowest frequency LED (red). The frequencies of Alpha and Theta are in between Beta and Delta, and so they get LEDs with frequencies in between those used for Beta and Delta. This makes it easier for the user's brain to entrain to each brainwave type, even if the four brainwave types are fading in and out independently. The reason that there are four colors, one for each brainwave type, is that this makes it easier for the user's brain to entrain to each brainwave type, even if the four brainwave types are fading in and out independently.

The combination of the four binaural beats, each with its own brainwave type, and the four different LEDs, each with its own brainwave type, with the sound and light in phase with each other, makes it very easy for the user's brain to track what is going on, and thus it is very easy for their brain to entrain to the sequences presented by the GuideGlasses.

The software follows a brainwave sequence from a session file. The session file gives a sequence of brainwave types, with the duration to play each brainwave type. The session file can also tell the software to bend the audible pitches, as well as slow down the sequencing. See the listing for mitch—OJ.ses, later in this document for an example of a session file for a short meditation sequence. The following session files are listed later in this document:

mitch_03.ses a short meditation sequence
mitch_04.ses a longer meditation sequence sleepl.ses a sequence for going to sleep
wake-up.ses a sequence for waking up There is currently no session file for going back to sleep, but this sequence will be similar to a combination of the waking up sequence followed by the going to sleep sequence (since my experiments show that it is important for the person who woke up to be fully awake in order to more easily go back to sleep).

The session files have 4 commands: HOLD, FADE, TEMPO, and BEND, as well as comments.

HOLD has one argument, which is the time in seconds with no change to the outputs of the GuideGlasses.

FADE contains up to 5 arguments. The first argument is the number of seconds to perform the fade in or fade out. Then there are up to 4 arguments, one for each brainwave type: Beta, Alpha, Theta, Delta (in that order). Each of these arguments is the amplitude to fade each brainwave type up or down.

TEMPO contains 3 arguments. The first argument is always 0. The second argument is the amount of increase or decrease of the tempo, and the third argument is the number of seconds to take to shift the tempo up or down.

BEND contains 3 arguments. The first argument is always 0. The second argument is the amount of increase or decrease of the pitch bend, and the third argument is the number of seconds to take to shift the pitch up or down.

These session files can be converted to a form that can be used by the Z8 firmware by using GG.exe The firmware as it stands has a bug in the LED pus ling algorithm that needs to be fixed. It pulsing is not sinusoidal for low amplitudes for a given brainwave type. Also, the firmware currently does not support TEMPO or BEND. All of this will be implemented in the finished product.

Below is a description of the GuideGlasses hardware, followed by a description of the firmware, followed by a listing of the firmware. Then there is a listing of the sample session files. Finally there is a listing of the C language development software and utility programs.

GuideGlasses Hardware

Figure 3:
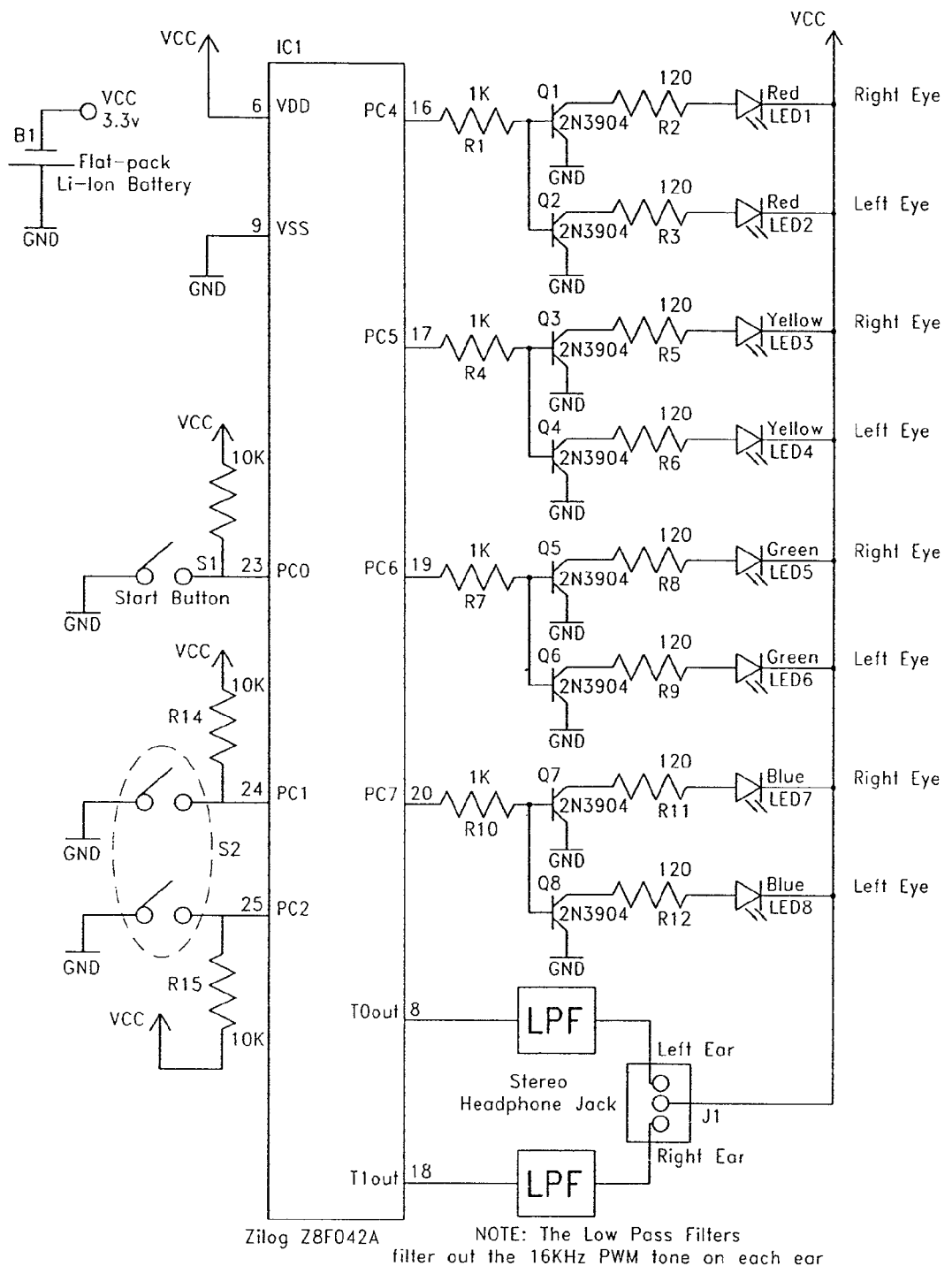
FIG. 3 is a schematic showing the configuration of a different embodiment of the "Guide Glasses" embodiment of the invention.
Figure 4:
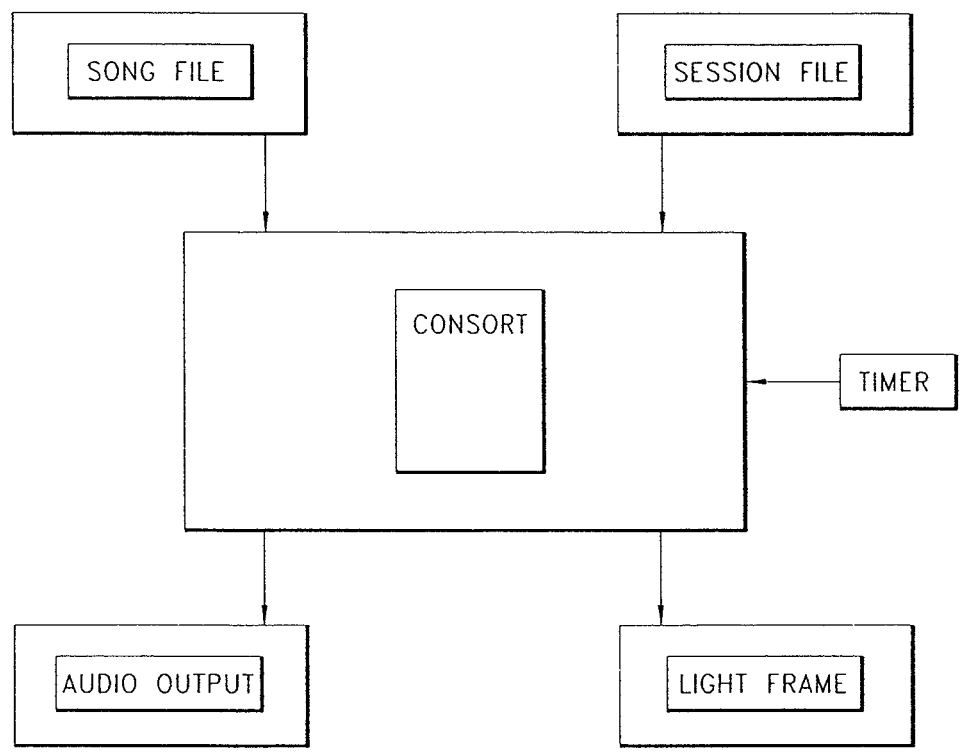
FIG. 4 shows a Guide Glasses firmware system diagram.
Figure 5:
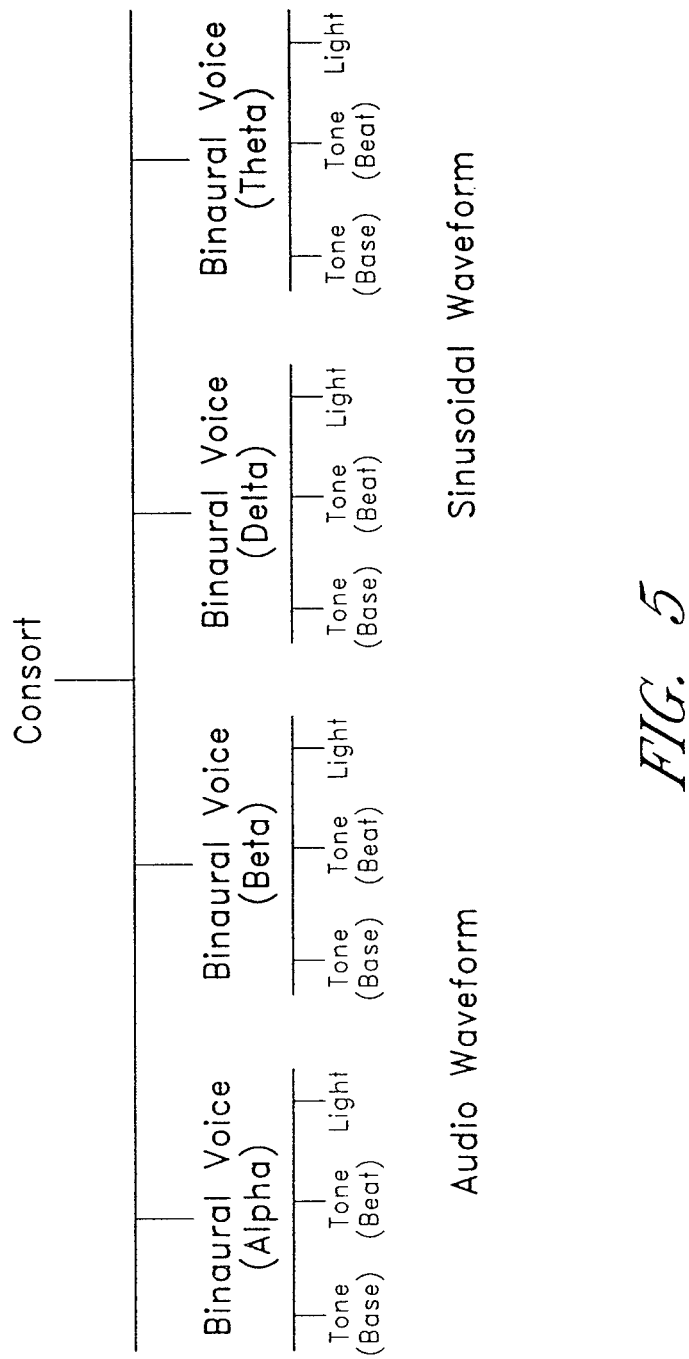
FIG. 5 shows the hierarchy of software objects in the Guide Glasses embodiment.

Refer to the schematic diagram shown in FIG. 3. The hardware is controlled by a 20 MHz Zilog Z8 microcontroller that has two timers each with PWM (Pulse Width Modulation).

There are four outputs for the sinusoidally pusling LEOs. Each of these outputs controls two LEOs, one for the right eye and one for the right eye. So, there are a total of 8 LEDs, LED I through LED8, each with its own transistor driver, consisting of Q I through Q8 and R 1 through R 12.

The sound comes from the two timers set up for PWM with a 16 KHz carrier. Each ear has a Low Pass Filter to filteer out the 16 KHz, leaving the useful audio content, which is all below 8 KHz.

S 1 is a momentary push button switch that starts a given sequence, chosen by the user with S2. S2 can choose 4 different sequences: Go to Sleep, Go Back to Sleep, Wake Up, and Meditate.

The hardware is powered by a rechargeable Li-Ion flatpack battery. This battery is very light weight, and recharges quickly.

The electronics is mounted on a flex circuit that is sewed into a comfortable sleep-mask that wraps around the user's head, covering their eyes and ears with convex cups. The sleep-mask is soft and flexible, with a Velcro strap to enable people with different sized heads to wear it comfortably, even if they fan asleep wearing the device, and even if the user tosses and turns in their sleep.

The Nature of the Audio Waveform

The audio waveform is kept as an array of signed 8-bit values, and is organized such that the last element can serve as the predecessor of the first element For example, a triangle waveform with an amplitude of 4 and period of 8 would be stored as the values (0, 2, 4, 2, 0, −2, −4, −2).

In practice the waveform is a digitized sample of an instrument playing a constant note, recorded over a period of perhaps a second. This sample is then digitally pre-processed in order to create a seamless aural connection between the beginning and end of the waveform.

The sample rate used to record the instrument, and the pitch of the note played by the instrument are kept as the constants sample Jate, and original yitch.

The Calculation of Pitch

If the waveform array is traversed one element at a time, and the value of each element is sequentially fed, at a rate equal to the original sample rate, into a D/A converter that is connected to an appropriate amplifier/speaker, then the original pitch will be sounded. If the waveform array is traversed 2 elements at a time (that is, we first select element 0, then element 2, etc.), then a pitch of double the original frequency is sounded. Let us denote the traversal rate as playbackJate, and the number of elements traversed each time as step. Then, in general:

$$pitch = step * (Pla.vback\_rate/s8/JIple\_rate) * original.\_pitch$$

Or, what is more useful, if we wish to playa tone at any given pitch, then we need only calculate the corresponding step by which to traverse the array.

$$step = (sample\_rate/pla.vback\_rate) * (desiredyitch/original\_pitch)$$

The Tone Object

The Tone Object maintains state information which is used to sound a tone at a specific pitch. The state variable index holds the tone's current position within the waveform alTay. The state variable step is the amount by which to increment index at each iteration. Both are real numbers. At startup, index is set to 0 and step is calculated from the initial pitch desired. As index is incremented by step during successive iterations it will eventually exceed the size of the waveform array. At this point index is "wrapped" by subtracting the array size from itself.

A third state variable, value, contains the current aural value of the tone, as referenced by index, i.e.: waveform—array[index]. Since index is almost certainly not integral, we take the value of the closest element, or average the two closest elements, in order to mitigate aliasing effects.

The Light Object

The Light Object maintains state information used to produce a light which pulsates regularly (at the rate of its associated brainwave frequency). It does this by referencing the Sinusoidal Waveform, with an index which is incremented each iteration by step. The value of step is initially calculated from the brainwave frequency associated with the Light Object. The value of the referenced sinusoidal waveform element is considered to be an illumination percentage, which is converted into a pulse-width value and used to drive the Light Object's respective LED in the Light Frame.

The Binaural Voice Object

The Binaural Voice Object is used to produce a binaural beat while playing a single part in a four part song. Each binaural voice has an associated brainwave: alpha, beta, delta, or theta.

The Binaural Voice Object consists of two Tone objects, the Base_tone and the Beat_tone, and a Light object. A state variable beat frequency is set at startup to the frequency of the voice's associated brainwave. When the Binaural Voice is instructed to play a given note ("A" for example), the pitch of the Base_tone is set to the corresponding frequency (440 Hz), and the pitch of the Beat_tone is set to this frequency plus the frequency of the associated brainwave (440 Hz+beat frequency).

When the part changes notes the process is repeated. Since a change of pitch in a Tone object consists merely in computing a new step value without disturbing the value of index, the note being sounded by the Binaural Voice can be freely changed without affecting the phase or continuity of the binaural beat.

The Consort Object

The Consort Object consists of four Binaural Voice objects (one for each of the brainwave frequencies), which it uses to play a four part song, as described in the song file, while temporally altering the intensity of the binaural beats in a specific way, as described by the session file.

The Song File

A song file is a list of variable-length records, implicitly ordered by time (i.e., the 1 st note of measure I comes before the 2nd note of measure I), describing the pitch of a note, its duration, and which voice to ascribe it to. When the end of the song file is reached, the referencing process resets its pointer to the beginning of the file, and repeats the song until the session is ended.

The song records contain the step values which generate the pitch of the corresponding note, for both the "Base" Tone and the "Beat" Tone.

The Session File

The session file is a list of records, implicitly ordered by time, describing the intensity of the binaural beats, and how the intensity of each should vary over time. For example, an initial record of (0, 20, 10, 30, 50) means "set the initial intensity of the alpha binaural beat to 20%, the beta beat to 10%, the delta beat to 30%, and the theta beat to 50%." A subsequent record of (15, 5, 20, 10, 40) means "over the next 15 seconds fade the intensity of the alpha beat to 5%, the beta beat to 20%, the delta beat to 10%, and the theta beat to 40%." When the last record is processed, the session is terminated.

Algorithmic Flow

The execution of the algorithm occurs in two phases. The 1st phase occurs in mainline code at startup, wherein the various state variables and pointers are initialized. Once this has occurred the algorithm is executed iteratively under interrupt, triggered by a timer whose reset value is equal to the audio playback rate. Thus each iteration of the algorithm produces at least a new audio output.

Development Software & Utilities

The firmware for the device was developed initially by writing a C language program that runs on DOS on a PC. The source file for this software is GG:c.

The wavfreq.c utility is used to add a proprietary chunk to a standard. W A V file. This chunk saves the frequency of the note recorded in the wave file. This information is used by the C version of the GG.c program to initialize the original yitch state variable. The wavinfo.c utility displays this chunk info on the PCs screen.

The source code for GG.c as well as wavfreq.c and wavinfo.c is included after the firmware listing.

Wavelength Involution

In certain embodiments, a firmware technique, termed "Wavelength Involution" can be applied by which a digital audio sample, when used in tone generation, is processed in a way that increases its "ambient" or "natural" quality, without disturbing the phase or frequency of the generated tone.

When a short digital sample ("the waveform") is used to generate a tone it can produce two aesthetically undesirable effects:

A) The change in timbre and harmonic content over the length of the waveform is heard as a repetitive, unmusical "wah," or aural cycle, within the generated tone.

B) When the pitch of the generated tone changes, the rate of the aural cycling within the tone increases or decreases in proportion to the pitch change, producing a further unnatural effect.

The objective of Wavelength Involution is to mitigate these effects by:

A) Varying the rate of aural cycling within a tone over time in a musical way.

B) Making the rate of aural cycling in a tone independent of its pitch.

As described in the section entitled "The Calculation of Pitch" (hereinabove) a tone at a given pitch is generated by traversing the waveform array using a calculated step:

$$step = (sample\_rate/playback\_rate) * (desired\_pitch/original\_pitch)$$

If num_sample_pts denotes the number of elements in the waveform array, then the aural cycling rate for a tone at a given pitch is:

$$aural\_cycling\_rate = (step * playback\_rate)/num\_sample\_pts$$

As an illustrative, but non-limiting, example, some typical numbers can be assigned to the various parameters, as they can be found in an actual implementation of a sound and light machine, to discover what this rate is in practice:

sample_rate=22050
playback_rate=18000
original_pitch=1600
num_sample_pts=4000

If we generate a tone at a pitch of G5 (the G an octave above "middle C"), or 783.99 Hz, the step will be, 6002, producing an aural cycling rate of 2.7 Hz. If we then change the tone's pitch to B4 (the B above "middle C"), or 493.88 Hz, the step becomes 0.3781, and the aural cycling rate is 1.7 Hz.

This fixed, repetitive aural cycling within the tone at 2.7 Hz or 1.7 Hz fatigues the ear, and the abrupt jump between the two rates when the tone changes pitch seems "unnatural"

The principle behind Wavelength Involution ("A turning inwards, a retrograde change") is to periodically decrement the tone's index into the waveform array by a value of exactly one (original) wavelength. This change is orthogonal to the incremental additions of step that are made to the index at each iteration during playback. The effect of this involution is to lengthen the amount of time it takes for the waveform array to be traversed, thus lengthening the aural cycle in the corresponding generated tone.

The following concrete example illustrates the concept.

First, an additional parameter is needed, the wavelength of the waveform, This is given by wavelength=sample_rate/original_pitch In this example, the wavelength is 13.78125

This means that if the nth wavelength in the waveform starts at position waveform[x], then the next wavelength starts at position waveform[x+13.78125] and the prior wavelength at [x−13.78125]. (Of course, the waveform array is discrete, so to resolve the waveform value at a non-integral indice, interpolation is used).

During the normal course of operations a tone will be generated by adding the tone's calculated step to its index position into the waveform array, once pei iteration during playback. If we are generating a G5 pitch, as in our example, and the tone's index is initialized to 0 at the start of playback, then the accumulated index into the waveform will change as per the following table.

| iteration | index |
|---|---|
| 1 | .6002 |
| 2 | 1.2004 |
| 3 | 1.8005 |
| ... | |
| 50 | 30.0100 |
| 51 | 30.6102 |

When the index reaches the end of the array (3999 in this example), it wraps back to 0 and continues. If we introduce a process ("involution") by which the value of the index is decremented by one wavelength every 50 iterations (the involution "period") than the accumulated index table looks like this:

| iteration | index |
|---|---|
| 1 | .6002 |
| 2 | 1.2004 |
| 3 | 1.8005 |
| ... | |
| 50 | 30.0100 − 13.78125 = 16.22875 |
| 51 | 16.8289 |

This lengthens the aural cycle by a factor of 30.0100/(30.0100−13.78125), producing in this case an aural cycling rate of 1.46

In general, if we denote the involution period by Inv_period, and the aural cycling rate of the involuted tone by Inv_cycle_rate, then for a tone at a given pitch:

Inv_cycle_rate=aural_cycle_rate*(Inv_period*step−Wavelength)/(Inv_period*step)

If we now pick 2 different involution periods, Inv_P1 and Inv_P2, and then vary the involution period being applied to the tone over time such that it moves gradually between Inv_P1 and Inv_P2, then the constant repetitive aural cycling of the uninvoluted tone is replaced by a shifting aural cycle not unlike that produced by the changing speeds of a rotary speaker.

Additionally, when the pitch of the tone changes, Inv_P1 and Inv_P2 can be scaled in proportion to the change in pitch, thus eliminating the abrupt change in the aural cycling rate that would otherwise occur in an uninvoluted tone.

It is important to note that this technique disturbs neither the phase nor the frequency of the generated tone, thus preserving the tone's ability to produce a steady binaural beat when paired with a detuned tone within a binaural voice. Thus, the technique can be applied without disturbing the effects of a sound and light machine produced in accordance with the present embodiments.

What is claimed is:

1. A sound and light machine (SLM) that produces sound and light pulses at brain wave frequencies that is programmed to induce a particular state of consciousness in a user, while simultaneously providing music to the user, comprising:
   a left and a right light emitting diode (LED), the LEDs configured to be placed in front of the user's left and right eyes, respectively, and programmed to pulse light at a frequency that helps induce the particular state of consciousness in the user;
   a left and a right headphone speaker, the speakers configured to play different tones into right and left ears to produce binaural beats that match the LED pulse frequencies;
   a microcontroller that runs firmware to control the LEDs and headphone speakers so as to produce a plurality of dominant brainwave frequencies; and
   a plurality of binaural voices corresponding to each of said dominant brainwave frequencies, each of said binaural voices comprising a base tone, a beat tone and an associated LED, said binaural voices configured to produce a melody of said music without interfering with the sound and light pulses at the brainwave frequencies, wherein the base tone is set to a frequency producing said melody and said beat tone is set to the frequency producing said melody plus a frequency of said brain wave frequencies of the sound and light pulses,
   wherein said melody comprises a plurality of notes, and is stored in a song file that comprises a list of variable-length records describing each note's pitch and duration, and
   wherein the firmware comprises information in a Tone Object comprising a state variable index holding one of the plurality of note's current position within a waveform array and a state variable step, which is an amount by which to increment the state variable index at each iteration, wherein the index is set to 0 at startup and the step is calculated from an initial note.

2. The SLM of claim 1, wherein the dominant brain wave frequencies comprise four dominant brainwave frequencies and the binaural voices comprise four binaural voices.

3. The SLM of claim 2, wherein the SLM comprises an eight voice digital synthesizer with embedded binaural capabilities and a synchronized light frame.

4. The SLM of claim 1, further comprising electronics and a battery which are embedded in a flexible housing that is housed in a soft and flexible mask that fits comfortably on a human head so as to cover the user's eyes and ears.

5. The SLM of claim 1, further comprising an authoring system (GG.c) that can specify a brain-entrainment session in a text file.

6. The SLM of claim 5, wherein the microcontroller is programed by a digital file that describes a waveform that applies a session of said brainwave frequencies to the music.

7. The SLM of claim 6, wherein the music comprises pre-calculated 24-bit step values for each note of the song file, and pre-calculated 24-bit fading coefficients for each change in binaural intensity of each of said plurality of voices.

8. The SLM of claim 7, further comprising a 20 Mhz 8-bit microprocessor, without a hardware divide, with 8K of ROM and 256 bytes of RAM.

9. The SLM of claim 8, wherein the SLM provides five separate brain entrainment applications.

10. The SLM of claim 9, wherein at least 45 minutes of generated binaural music using a complex waveform are provided at a playback rate of 18 Khz.

11. The SLM of claim 1, further comprising a serial port connector that writes the firmware into the microcontroller so as to permit programming of brain wave frequency sequences in the LEDs and headphone speakers.

12. The SLM of claim 1, further comprising graphics placed over each of said left and right LEDs.

13. The SLM of claim 1, wherein the SLM is programmed to fade sound and/or lights in and out.

14. The SLM of claim 1, wherein the SLM is programmed to handle multiple simultaneous frequencies.

15. The SLM of claim 1, wherein the SLM is programmed to match brain wave types to different colored LEDs and/or binaural base frequencies.

16. The SLM of claim 1, wherein the SLM is programmed to help people sleep or wake up.

17. The SLM of claim 16, wherein the SLM is configured to fit in a soft fabric sleep mask and use a light, flexible, rechargeable battery so as to be comfortable for sleeping.

18. The SLM of claim 1, wherein the SLM is programmed to help people meditate.

19. The SLM of claim 1, wherein the SLM is programmed to pulse the LEDs at a frequency selected from the group consisting of 2.2, 6.0, 11.1 and 14.4 Hz, in order to elicit delta, theta, alpha or beta waves, respectively.

20. A method of inducing a particular state of consciousness in a user while simultaneously playing music, comprising providing an SLM according to claim 1;
- placing the SLM such that the LEDs are in front of the user's eyes and the headphone speakers are near the user's ears; and
- turning the SLM on so as to run a sequence of frequencies designed to induce the particular state of consciousness while simultaneously playing the music provided to the user.

* * * * *